United States Patent [19]

Hung et al.

[11] Patent Number: 4,595,536
[45] Date of Patent: Jun. 17, 1986

[54] TRIPHENYLMETHANE DYESTUFF

[75] Inventors: William M. Hung; Jack M. Knox, both of Cincinnati, Ohio

[73] Assignee: The Hilton-Davis Chemical Co., Cincinnati, Ohio

[21] Appl. No.: 732,989

[22] Filed: May 13, 1985

Related U.S. Application Data

[62] Division of Ser. No. 560,000, Dec. 9, 1983, Pat. No. 4,536,368.

[51] Int. Cl.$^4$ .............................................. C09B 11/10
[52] U.S. Cl. .................................................. 260/394
[58] Field of Search ............................... 260/510, 394

[56] References Cited

U.S. PATENT DOCUMENTS

| | | | |
|---|---|---|---|
| 3,504,384 | 4/1970 | Radley et al. | 4/228 |
| 3,545,014 | 12/1970 | Davis | 4/228 |
| 4,200,606 | 4/1980 | Kitko | 422/37 |
| 4,248,827 | 2/1981 | Kitko | 422/37 |

Primary Examiner—Nicky Chan
Attorney, Agent, or Firm—Terrence E. Miesle; Thomas L. Johnson; Paul E. Dupont

[57] ABSTRACT

A method for sanitizing flush toilets wherein a sanitizing agent and a triphenylmethane dyestuff are dispensed into the toilet flush water. The dyestuff is resistant to attack by the sanitizing and therefore provides an aesthetically pleasing color to the water remaining in the bowl during the time period between flushes.

3 Claims, No Drawings

TRIPHENYLMETHANE DYESTUFF

CROSS REFERENCE TO RELATED APPLICATIONS our prior copending application and now This application is a division of application Ser. No. 560,000, filed Dec. 9, 1983, now U.S. Pat. No. 4,536,368.

BACKGROUND OF THE INVENTION (a) Field of the Invention

The present invention relates to the automatic sanitizing of flush toilets by means of dispensing certain water-soluble triphenylmethane dyestuffs and a sanitizing agent into the toilet bowl with each flush. The dyestuff is resistant to attack by the sanitizing agent and thus, provides color to the bowl water during the time period that the water remains in the bowl between flushes.

(b) Information Disclosure Statement

Automatically dispensed toilet bowl cleaning and/or sanitizing systems which contain colorants to provide a visual signal to the user that the sanitizing product is being dispensed are well known. There are two general types of these sanitizing systems available. One of these systems has a visual signal which is transitory, that is, the sanitizing solution in the toilet bowl retains its colored appearance for only a brief amount of time. The other system, and one in which this invention finds its utility, is the system wherein the sanitizing solution in the toilet bowl is intended to show persistent color until the next flush.

U.S. Pat. No. 3,504,384, which issued Apr. 7, 1970, discloses that the dyestuff known as Disulfide Blue VN150 can be incorporated into surfactant components contained within a dual compartment dispenser for automatically dispensing a hypochlorite solution and a surfactant solution into the toilet bowl during flushing. This dye, which is believed to be Disulphine Blue VN150 (Color Index 42045) having the formula

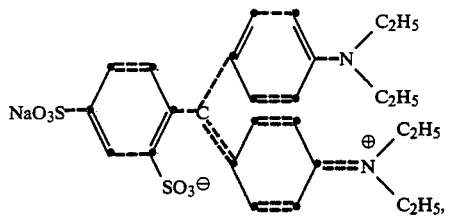

has been found to be resistant to oxidation to a colorless state by hypochlorite. But, solutions of this dye have a tendency to change from a blue shade to a reddish-purple shade upon prolonged contact with hypochlorite.

U.S. Pat. No. 4,200,606, which issued Apr. 29, 1980, discloses a method of treating a flush toilet, from a dual compartment dispenser for automatically dispensing, with a hypochlorite sanitizing solution and a surfactant solution each time the toilet is flushed. A persistent color is purportedly maintained in the bowl water by incorporating either FD&C Blue No. 1 having the formula

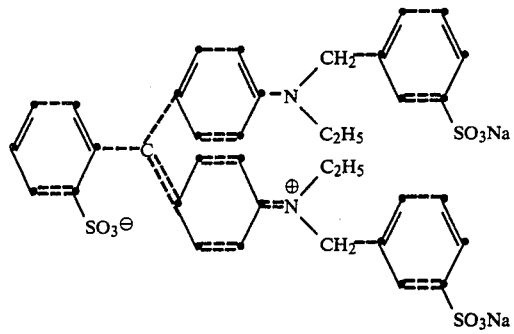

or FD&C Green No. 3 having the formula

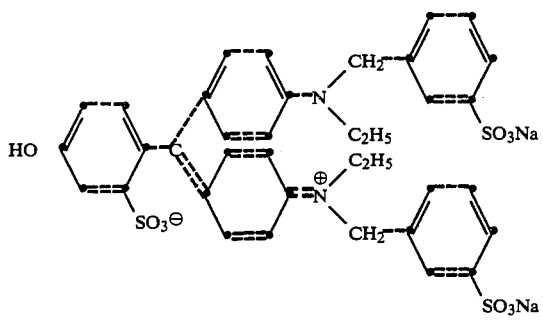

into the surfactant solution.

U.S. Pat. No. 4,248,827, which issued Feb. 3, 1981, discloses a method of treating a flush toilet each time it is flushed with a bromide-catalyzed hypochlorite sanitizing solution and a surfactant solution from a dual compartment dispenser for automatically dispensing the solution. A transitory visual signal is provided to indicate the activity of the sanitizing agent in the bowl by incorporating a dye selected from the group of those identified by the Color Index numbers 24401; 42040; 63010; 42085; 42675; and those having Color Index names Basic Blue 80, Reactive Blue 17 and Acid Blue 182 into the surfactant solution.

U.S. Pat. No. 3,545,014, which issued Dec. 8, 1970, discloses an automatic sanitizer for flush toilets which contains a blue dye known as Acid Blue 9 (Color Index 42090) stated to impart a blue color to the water in the bowl.

The most common sanitizing agent used in automatic toilet bowl sanitizers is a chemical compound which will generate hypochlorite ion in water. The hypochlorite ion is a strong oxidizing agent which makes it highly effective in bleaching stains, breaking down and removing soils and killing microorganisms, thereby providing effective sanitizing action to the toilet bowl. Although highly effective in bleaching stains, removing soil and killing microorganisms thereby providing effective sanitizing action in the toilet bowl, hypochlorite ion will also operate to bleach or oxidize any dye which is utilized as a colorant in the automatic toilet bowl sanitizers. In any toilet bowl sanitizing system which is designed to provide a persistent visual signal between flushes, which period is often up to six to eight hours or longer, any such system requires a dye which is resistant to attack by oxidizing agents such as hypochlorite and which will not be bleached to a colorless state or oxidized to a different and aesthetically displeasing shade or color. Currently known automatic toilet bowl sanitizers have been only partially successful in this regard and accordingly there is a need for an automatic toilet bowl sanitizing system which provides a stable visual color signal which persists for between six to eight hours between flushings.

SUMMARY OF THE INVENTION

It has now unexpectedly been found that certain triphenylmethane dyestuffs have superior resistance to attack by oxidizing agents, for example, hypochlorite and remain colored in the presence thereof for about eight hours. The present invention provides a method of sanitizing a toilet bowl wherein a sanitizing agent, a surfaceactive agent and a water-soluble triphenylmethane dyestuff, which is resistant to attack by the sanitizing agent, are automatically dispensed to the toilet bowl during flushing. The water in the bowl at the end of the flush, which remains in the bowl during the widely-varying time intervals between flushes, retains a persistent color with no shade or color shift because of the dyestuff's resistance to attack by the sanitizing agent.

In its chief aspect, the invention relates to a method of providing a visual color which persists in the toilet bowl water between flushes, that is, the color is resistant to bleaching by the sanitizing agent to a colorless state or oxidation to a different shade or color between flushes.

DETAILED DESCRIPTION OF THE INVENTION INCLUSIVE OF THE PREFERRED EMBODIMENTS

More specifically, this invention relates to a method of treating a flush toilet which comprises a flush tank and bowl, with a sanitizing agent each time the toilet is flushed and providing a persistent color to the bowl water between flushes, said method comprising the step of dispensing into the flush water an aqueous solution which contains (A) a sanitizing agent, and (B) a triphenylmethane dyestuff selected from the group having the formula

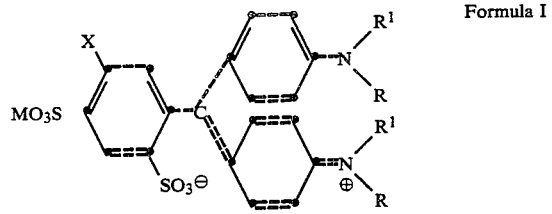

Formula I in which R represents benzyl optionally substituted in the benzene ring by $SO_3M$ in which M represents an alkali metal cation, an ammonium ion or an alkaline earth metal cation; $R^1$ represents a non-tertiary $C_1$ to $C_4$ alkyl; and X represents hydrogen or hydroxy.

In a particular embodiment, the invention sought to be patented resides in a method of treating a flush toilet which comprises a flush tank and bowl, with a sanitizing agent each time the toilet is flushed and providing a persistent color to the bowl water between flushes, said method comprising the step of dispensing from separate dispensing means, into the flush water; (A) an aqueous solution of a sanitizing agent, and (B) a solution of a triphenylmethane dyestuff having Formula I hereinbelow.

Within the ambit of the particular embodiment of the invention is the method of treating a flush toilet wherein solution B contains a triphenylmethane dyestuff having the formula

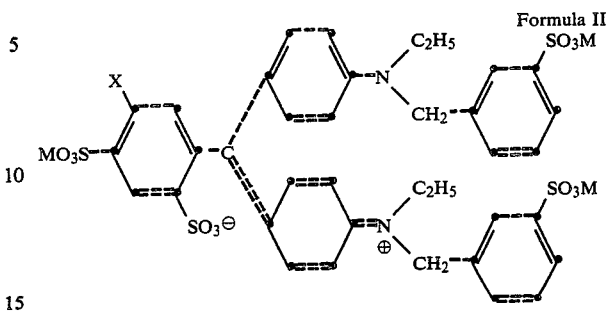

Formula II in which M and X have the same respective meanings given in Formula I.

A preferred sanitizing agent for use in the first particular embodiment is a sanitizing agent which produces hypochlorite ions in aqueous solution.

In a second aspect, the invention sought to be patented resides in the novel triphenylmethane dyestuffs of Formula II.

As used herein the term "non-tertiary $C_1$ to $C_4$ alkyl" denotes saturated monovalent straight or branched aliphatic hydrocarbon radicals including methyl, ethyl, propyl, isopropyl, butyl, isobutyl and the like.

As used herein the term "alkali metal cation" includes lithium, sodium and potassium cations.

As used herein the term "alkaline earth metal cation" includes magnesium and calcium cations.

The sanitizing agent which can be used in the practice of the present invention is any compound which will effectively clean and/or sterilize the bowl of the toilet. The preferred sanitizing agents which can be used, and to which the colorant is resistant to attack, are compounds which exhibit germicidal or disinfectant properties and which have oxidizing characteristics, that is, are ones which generate oxygen or hypochlorite ion in an aqueous solution. Compounds included within this group which generate oxygen are the alkali metal and alkaline earth metal salts of the peroxy acids such as perborates, percarbonates, peroxides and persulfates.

Compounds included within the group which generate hypochlorite ion in aqueous solution are the alkali and alkaline earth metal hypochlorites, hypochlorite addition products, chloramines, chlorimines and chloramides. Specific examples of this type of compound are: sodium hypochlorite, potassium hypochlorite, lithium hypochlorite, calcium hypochlorite, calcium hypochlorite dihydrate, monobasic calcium hypochlorite, dibasic magnesium hypochlorite, chlorinated trisodium phosphate dodecahydrate, potassium dichloroisocyanurate, sodium dichlorocyanurate dihydrate, 1,3-dichloro-5,5-dimethylhydantoin, N-chlorosulfamide, Chloramine T, Dichloramine T, Chloramine B and Dichloramine B. Also, free acids such as trichloroisocyanuric acid may be used as a source of hypochlorite. The hypochlorite ion generating compounds are particularly preferred as sanitizing agents in the automatic toilet bowl cleaners because they are relatively inexpensive and exhibit a high degree of sanitizing strength per unit weight. The amount of oxidizing agent such as, hypochlorite-providing compound, dispensed into the toilet by the so-called automatic bowl cleaner may vary, but it is preferred that the amount released be sufficient to provide from approximately 0.5 parts per million to approximately twenty parts per million of available chlorine or the equivalent thereof in the bowl water after completion of the flush.

Another effective sanitizing agent is oxalic acid.

Essential to the method of the instant invention is the use of a water-soluble, bleach resistant dye of Formula I which is sufficiently resistant to oxidation that the solution of the dye in the toilet bowl will not be oxidized to a different shade or color or to a colorless state by the oxidizing agent in the bowl for a time period of from six hours to approximately eight hours, typically the maximum time interval between flushes in the average household.

The dyes of Formula I are not completely stable to attack by the oxidizing agent; however, they are sufficiently resistant to attack to adequately serve as colorants for use in automatic toilet bowl cleaners. When there is a long time interval between flushes, there will be some fading of the color in the bowl water due to the slow attack by the oxidizing agent on the dye, but the water will not change color or shade, nor will it become colorless.

The amount of dye which is dispensed into the water of the toilet bowl is dependent on the color intensity desired and the amount of sanitizing agent dispensed by the automatic cleaner. In general, the amount of dye dispensed by the automatic cleaners will vary between approximately 0.05 parts per million to approximately 10 parts per million in the water of the toilet bowl after the flushing is completed.

The triphenylmethane dyes of Formula I are readily prepared by procedures well known in the dyestuff art. General methods for the preparation of triphenylmethane dyestuffs from benzaldehydes and derivatives of aniline are taught in (a) FIAT Final Report No. 1313 and (b) PB Report 85172, pages 351-352.

Two of the preferred triphenylmethane dyestuffs of Formula I which are useful in the present invention have the formulas

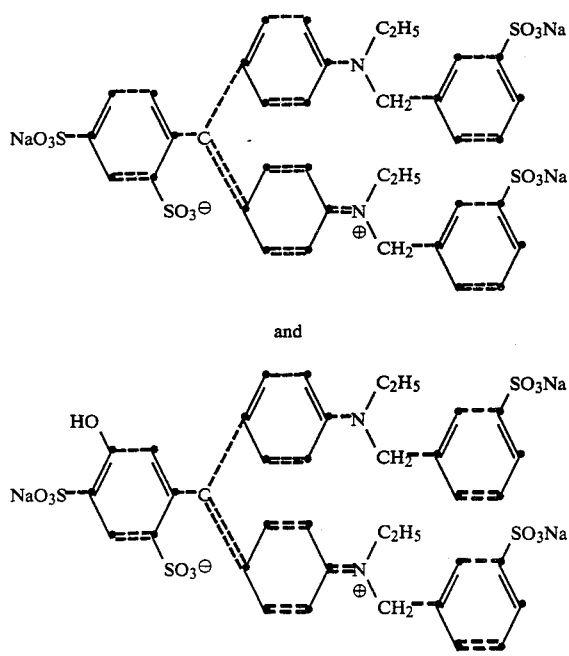

Surface active agents are usually added to the automatic sanitizers because these agents enhance the sanitizing performance by breaking up and emulsifying the soils present in the bowl, and further, the sudsing action caused by these agents is aesthetically desirable.

The surface active agents are generally combined with a dyestuff of Formula I and an inorganic salt which may also serve as a sequestering agent or a pH control agent but, in any event, the inorganic salt aids in dissolving the dye and the surface active agent. Optionally, a perfume may be added to this composition to provide a pleasant smell to the area surrounding the toilet and also to help mask the hypochlorite odor of the hypochlorite-type of sanitizing agent. The compositions containing the dye of Formula I, the surface active agent and other optional components are generally prepared in the form of a cake which is conveniently placed into one of the compartments of the dispensers designed to receive said cake of solid material. The cake can be prepared by pouring a melt of the composition into a mold and solidifying the composition by cooling. Alternatively, the cakes can be prepared by extrusion or hydraulic stamping.

Surface active agents operable in compositions suitable for use in practicing the present invention can be selected from the broad groups known as nonionic and anionic agents, ampholytic, zwitterionic and cationic surface active agents. One group of nonionic surface agents which can be utilized in the present invention is the alkylene oxide condensates which are broadly defined as compounds produced by the condensation of alkylene oxide groups (hydrophilic in nature) with an organic hydrophobic compound. One example of such alkylene oxide condensates are the products of aliphatic alcohols with ethylene oxide. The aliphatic alcohol generally has an alkyl chain which can be either straight or branched and contains from about eight to about twenty-two carbon atoms. An example of ethoxylated alcohols include the condensation of ethylene oxide with tridecanol. An example of a commercially available nonionic surface active agent of this type is Emulphogene® TB-970 (GAF Corp.). Other products of varying carbon chain length of the aliphatic alcohols and the number of moles of ethylene oxide per mole of alcohol can be used. Other examples of commercially available nonionic surface active agents are Neodol® 25-9 (Shell Chemical Co.) and Tergitol® 15-S-12 (Union Carbide Corp.). Other nonionic surface active agents which can be used in the present invention include the polyethylene oxide condensates of alkyl phenols; the condensation products of ethylene oxide with the product resulting from the reaction of propylene oxide and ethylene diamine; the ammonia, monoethanol and diethanol amides of fatty acids having an acyl moiety of from about 8 to about 18 carbon atoms; and the semi-polar nonionic surface active agents, for example, amine oxides, phosphine oxides and sulfoxides. Cationic surface active agents which are useful in the present invention are the quaternary ammonium compounds, for example, coconut dimethyl benzyl ammonium chloride. Examples of anionic surface active agents are the water-soluble alkali metal salts of organic sulfonic acid reaction products such as the sodium or potassium salts of sulfonated $C_8$ to $C_{18}$ alcohols and glyceride sulfonates.

The dispensing means which operate to dispense the sanitizing agent and dye-surfactant can be either a single dispensing or dual dispensing type. In the dual dispensing type, the sanitizing agent and the dye-surfactant are dispensed from separate containers. Such devices are known in the art, for example, as described in U.S. Pat. Nos. 3,504,384; 4,200,606; 4,248,827; 4,249,274; and 4,353,866. There are several commercial automatic toilet bowl sanitizers on the market which are dual dispensing devices.

The dispensing means which operate to dispense a single solution containing the sanitizing agent, dye and surfactant is a single dispenser. Such devices are known in the art, for example, as described in U.S. Pat. Nos. 3,698,021; 3,604,020; 4,305,162; and 4,375,109. There are numerous commercial automatic toilet bowl sanitizers on the market which are single dispensing devices.

The longevity of the dyestuff color in the sanitizing solution was measured by simulating the conditions which exist in the toilet bowl after the flushing cycle was completed when an automatic toilet bowl sanitizer was used. Solutions were prepared which contained 2.5 parts per million of dyestuff, 40.0 parts per million of a surface active agent and 40.0 parts per million of sodium sulfate. After an initial visible spectrum reading was taken, sufficient sodium hypochlorite solution or trichloroisocyanuric acid solution equal to 10.0 parts per million of available free chlorine was added to the dyestuff solution and spectrophotometer readings were taken automatically at specified pre-set time intervals depending on the dyestuff tested and the sanitizing agent employed. The dyestuffs of this invention were compared with FD&C Blue No. 1 and FD&C Green No. 3, the dyestuffs disclosed in U.S. Pat. No. 4,200,606, for the length of time the color persisted in the simulated bowl water.

A simple qualitative test for the persistence of the dyestuffs of Formula I in the presence of a sanitizing agent was carried out by dissolving the dyestuff in distilled water and adding sufficient dyestuff solution to one liter of distilled water thereby adjusting the resulting solution to the same visual strength as a solution of FD&C Blue No. 1. One such solution served as a control and another was treated with sufficient sanitizing agent to give a concentration of 10.0 parts per million in the sanitizing solution. The persistence of color in the presence of sanitizing agent was determined visually by comparison with the control. In testing for the longevity of the dyestuff color in the presence of hypochlorite-ion-generating sanitizing agents, three solutions were prepared in this manner, one a control, and the remaining two solutions were tested with sanitizing agents. One was tested with a solution of trichloroisocyanuric acid, and the second with sodium hypochlorite solution. The amount of hypochloriteion-generating sanitizing agent was added to 10.0 parts per million of available chlorine in the dilute dyestuff solution. The amount of dyestuff remaining in the solution was visually observed and compared to the control.

In order to carry out direct use tests, the dual dispensing devices for the dye-containing surface active agent cake and the sanitizing agent cake were prepared to simulate commercially available dispensers. Thus, a commercial cake of trichloroisocyanurate was used in conjunction with a prepared surface-active agent cake containing a dyestuffs of Formula I. The dual dispenser device was then tested in a flush toilet by inserting it into the tank. The persistence of the color of the bowl water and staining effects were observed after several flushes with intermittent periods of standing between flushes.

In order to carry out direct use tests, the dual dispensing devices for the dye-containing surface active agent cake and the sanitizing agent cake were prepared to simulate commercially-available dispensers. Thus, a commercial cake of trichloroisocyanurate was used in conjunction with a prepared surface-active cake containing a dyestuff of Formula I. The dual dispenser device was then tested in a flush toilet by inserting it into the tank. The persistence of the color of the bowl water and staining effects were observed after several flushes with intermittent periods of standing between flushes.

The persistence of the triphenylmethane dyestuffs of Formula I in the presence of oxidizing agents and, in particular, in the presence of hypochlorite was compared with that of the prior art triarylmethane dyestuffs, namely, FD&C Blue No. 1 (C.I. 42090) and FD&C Green No. 3 (C.I. 42053) under conditions which simulate those existing in a toilet bowl after the flushing cycle is completed as well as in the actual toilet bowl tests. The procedures employed are described in the comparative examples.

PREPARATIVE EXAMPLE I

With stirring, 50.0 g of concentrated sulfuric acid and 348.6 g of 83.6 percent N-ethyl-N-benzylaniline sulfonic acid were added to a mixture of 164.0 g of the disodium salt of 2,4-disulfobenzaldehyde and 500.0 ml of water. The reaction mixture was maintained at reflux temperature for approximately twenty-four hours and cooled to obtain a solution of {(2,4-disulfophenyl)-bis[N-ethyl-N-(3-sulfobenzyl)aminophenyl]}methane.

B. To the solution from part A above, there was added 570.0 ml of water and 55.2 g of oxalic acid dihydrate and the resulting solution was stirred approximately thirty minutes. To the solution, there was added dropwise over approximately twenty minutes, 63.2 g of 70 percent sodium dichromate at ambient temperature. The temperature gradually rose to approximately 37° C. After approximately fifteen minutes, the reaction mixture was heated to approximately 70° C. and maintained for approximately thirty minutes before cooling to ambient temperature. After setting overnight at ambient temperature, the reaction mixture was heated to approximately 70° C. and maintained for approximately one hour. Sufficient 10 percent sodium hydroxide was added slowly to the reaction mixture to set the pH at 7.0 and the resulting mixture was maintained at approximately 70° C. for approximately one hour. Then, 47.2 g of calcium chloride and 84.0 g of barium chloride dihydrate were added to the reaction mixture while maintaining a pH between 6.5 and 7.0 by adding 50 percent sodium hydroxide, as needed. The resulting mixture was filtered and the filtercake washed with two 250.0 ml portions of water. The clear blue filtrate and wash was combined and spray dried to obtain 496.3 g of dark blue solid containing the dyestuff

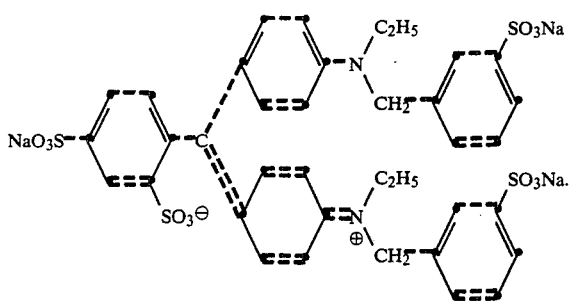

The visible spectrum of a water solution of the blue solid had a significant adsorption at 639 millimicrons.

PREPARATIVE EXAMPLE II

A. A mixture of 348.6 g of 83.6 percent N-ethyl-N-benzylaniline sulfonic acid, 500.0 ml of water, 5.5 ml of concentrated sulfuric acid and 52.7 g of 95 percent 3-hydroxybenzaldehyde was stirred at reflux temperature under a nitrogen atmosphere for approximately 22 hours. Then, 500.0 ml of water was added slowly to the reaction mixture and it was cooled to ambient temperature. The supernatant liquid was poured from the resultant hard mass of solid. To the solid, there was added 1.0 liter of water and 55.0 ml of 50 percent aqueous sodium hydroxide. The resulting mixture was warmed gradually and stirred manually until all of the solid dissolved. The resulting alkaline solution was added dropwise with stirring to a solution of 90.0 ml of concentrated hydrochloric acid and 3.0 liters of water. The pale green solid which formed was collected by filtration, washed twice each time with 500.0 ml of water, and dried to obtain 308.0 g of {bis[4-N-ethyl-N-(3-sulfobenzyl)aminophenyl]-(3-hydroxyphenyl)}methane, a pale green solid which melted over the range of 260° to 270° C.

B. With stirring, 35.0 g of the product from Part A above was added in small portions over approximately three hours to 150.0 g of 20 percent oleum while maintaining a temperature lower than 55° C. The reaction mixture was heated at approximately 70° C. for one hour and at a temperature between 75° and 85° C. for approximately four hours. The reaction mixture was poured slowly with stirring into 500.0 ml of 10 percent aqueous sodium sulfate solution. A brown tar-like mass resulted which settled to the bottom. The aqueous layer was decanted and set aside while the tar-like mass was dissolved in 50.0 ml of hot water. To the decanted water layer, there was added slowly 100.0 ml of 50 percent aqueous sodium hydroxide while maintaining a temperature below 30° C. A tar-like mass settled from the solution and was isolated by decanting and discarding the supernatant water layer. This second tar-like mass was dissolved also in 50.0 ml of hot water and the two solutions containing the dissolved tar-like solids were combined and diluted with an additional 70.0 ml of water. The pH of the aqueous solution was adjusted slowly from 1.1 to 3.9 by adding dropwise 50 percent aqueous sodium hydroxide. With stirring, 7.0 g of oxalic acid and 8.0 g of 70 percent aqueous sodium dichromate solution were added to the solution. The resulting mixture was heated to approximately 70° C. and the pH adjusted to 7.0 with the gradual addition of 50 percent aqueous sodium hydroxide. The temperature was maintained at approximately 70° C. for an additional hour. The resulting green solution was filtered through diatomateous earth to remove a trace of insolubles to obtain 258.0 g of green solution. The solution was spray dried to obtain 50.1 g of solids which contain the dyestuff having the structure

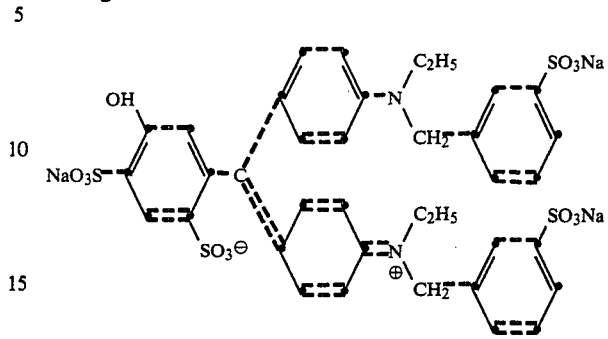

The visible spectrum of a sample of the solid dissolved in water exhibited a maximum at 637 millimicrons.

COMPARATIVE EXAMPLE 1

A. To approximately 1.0 liter of distilled water adjusted to a pH in the range of 8.0 to 8.5 with dilute sodium hydroxide solution, there was added 3.7 ml of a solution of 1.0 g of FD&C Blue No. 1 dissolved in 1.0 liter of distilled water. To the resultant dyestuff solution 4.0 ml of a solution consisting of 10.0 g of a surface active agent (Emulphogene ® TB-970, GAF Corp.) and 10.0 g of sodium sulfate dissolved in 1.0 liter of distilled water was added.

B. The visible spectrum of a sample of the solution from Part A above was recorded with a Perkin-Elmer Lambda ® 5 UV/VIS Spectrophotometer. To the solution from Part A above, 2.0 ml of a solution consisting of 1.0 ml of 5.0 percent active sodium hypochlorite dissolved in 9.0 ml of distilled water was added and immediately after a brief mixing, the visible spectrum of a sample of the mixed solutions was recorded with the spectrophotometer. Subsequent readings were taken and recorded automatically by the instrument at several time intervals as indicated in Table I hereinbelow. The spectrophotometer readings were obtained as the absorbance of the major wavelength of the dyestuff solution. These readings were converted for ease of communication to percentages by dividing the absorbance obtained at the time intervals after the addition of the sodium hypochlorite solution by the absorbance of the dyestuff solution obtained prior to the addition of the sodium hypochlorite solution. The percentages of dyetuff remaining are indicated in Table I hereinbelow. This procedure was used also in the subsequent tables.

TABLE I

| FD&C Blue No. 1 | |
|---|---|
| Elapsed Time (Minutes) | Percent Color Remaining in Presence of Sodium Hypochlorite |
| 0 | 100.0 |
| 2 | 99.5 |
| 4 | 96.0 |
| 64 | 71.0 |
| 124 | 47.0 |
| 184 | 25.0 |
| 244 | 11.0 |
| 304 | 3.0 |

C. To a second solution prepared in a manner similar to that described in Part A above, 11.0 ml of a solution consisting of 1.0 g of 88 percent active trichloroisocyanuric acid dissolved in 1.0 liter of distilled water was added and the visible spectrum of a sample was recorded as described in Part B above as indicated in Table II hereinbelow.

TABLE II

FD&C Blue No. 1

| Elapsed Time (Minutes) | Percent Color Remaining in Presence of Trichloroisocyanuric Acid |
|---|---|
| 0 | 100.0 |
| 4 | 84.0 |
| 14 | 49.0 |
| 24 | 32.0 |
| 34 | 26.0 |
| 44 | 23.0 |
| 54 | 22.2 |
| 64 | 22.2 |
| 74 | 22.2 |
| 84 | 22.2 |

The shade of the solution slowly shifted toward the red end of the visible spectrum.

COMPARATIVE EXAMPLE 2

Following the procedure described in Part A of Comparative Example 1, a dyestuff solution was prepared substituting 1.5 ml of a solution containing 1.0 g of FD&C Green No. 3 dissolved in 1.0 liter of distilled water adjusted to pH 8.0 to 8.5 using a dilute solution of sodium hydroxide for the solution of FD&C Blue No. 1. Parts B and C of Comparative Example 1 were repeated using the FD&C Green No. 3 solution. The test results are indicated in Tables III and IV hereinbelow.

TABLE III

FD&C Green No. 3

| Elapsed Time (Minutes) | Percent Color Remaining in Presence of Sodium Hypochlorite |
|---|---|
| 0 | 100.0 |
| 2 | 100.0 |
| 62 | 61.0 |
| 122 | 31.0 |
| 182 | 12.0 |

TABLE IV

FD&C Green No. 3

| Elapsed Time (Minutes) | Percent Color Remaining in Presence of Trichloroisocyanuric Acid |
|---|---|
| 0 | 100.0 |
| 2 | 88.0 |
| 12 | 46.0 |
| 22 | 35.0 |
| 32 | 29.0 |
| 42 | 24.0 |
| 52 | 22.0 |
| 62 | 19.0 |

No significant change in the shade of the solution was observed in the presence of sodium hypochlorite while the shade of the solution was observed to undergo a moderate shift to the red end of the spectrum after twelve minutes in the presence of trichloroisocyanuric acid.

EXAMPLE 1

The procedure described in the Comparative Example 1, Part A was followed except that the FD&C Blue No. 1 solution was replaced by 7.4 ml of a solution containing 1.0 g of the dyestuff prepared in Preparative Example I above dissolved in 1.0 liter of distilled water which had been adjusted to pH 8.0 to 8.5 using a dilute solution of sodium hydroxide.

Parts B and C of the Comparative Example 1 employing sodium hypochlorite and trichloroisocyanuric acid, respectively, were repeated with the above solution with the test results indicated in Tables V and VI hereinbelow.

TABLE V

Dye from Preparative Example I

| Elapsed Time (Minutes) | Percent Color Remaining in Presence of Sodium Hypochlorite |
|---|---|
| 0 | 100.0 |
| 2 | 99.0 |
| 62 | 85.0 |
| 122 | 74.0 |
| 182 | 64.0 |
| 242 | 55.0 |
| 302 | 48.0 |
| 362 | 43.0 |
| 422 | 41.0 |
| 482 | 42.0 |

TABLE VI

Dye from Preparative Example I

| Elapsed Time (Minutes) | Percent Color Remaining in Presence of Sodium Trichloroisocyanuric Acid |
|---|---|
| 0 | 100.0 |
| 18 | 70.0 |
| 19 | 69.0 |
| 34 | 58.0 |
| 49 | 50.0 |
| 64 | 44.0 |
| 79 | 39.0 |
| 94 | 36.0 |
| 109 | 32.0 |
| 124 | 30.0 |
| 139 | 28.0 |
| 154 | 26.0 |
| 169 | 25.0 |
| 184 | 24.0 |

There was no shift in the shade of the dyestuff solution. After a period of about five hours, approximately 16 times more dyestuff from Preparative Example I remained in the sodium hypochlorite sanitizing solution than the dyestuff identified as FD&C Blue No. 1. After a period of about one hour, 2 times more of the dyestuff from Preparative Example I remained in the trichloroisocyanuric acid sanitizing solution than the dyestuff identified as FD&C Blue No. 1.

EXAMPLE 2

Following the procedure described in Comparative Example 1, Part A above, a dyestuff solution was prepared using 6.0 ml of a solution containing 1.0 g of the dyestuff prepared in Preparative Example II above dissolved in 1.0 liter of distilled water adjusted to pH 8.0 to 8.5 using a dilute solution of sodium hydroxide in place of the FD&C Blue No. 1 solution.

Parts B and C of Comparative Example 1 employing sodium hypochlorite and trichloroisocyanuric acid, respectively, above were repeated using the solution prepared above. The test results are given in Tables VII and VIII hereinbelow.

TABLE VII

| | Dye from Preparative Example II |
|---|---|
| Elapsed Time (Minutes) | Percent Color Remaining in Presence of Sodium Hypochlorite |
| 0 | 100.0 |
| 2 | 96.0 |
| 62 | 86.0 |
| 122 | 84.0 |
| 182 | 83.0 |
| 242 | 83.0 |
| 302 | 83.0 |
| 362 | 83.0 |

TABLE VIII

| | Dye from Preparative Example II |
|---|---|
| Elapsed Time (Minutes) | Percent Color Remaining in Presence of Trichloroisocyanuric Acid |
| 0 | 100.0 |
| 2 | 78.0 |
| 47 | 73.0 |
| 92 | 73.0 |
| 137 | 73.0 |
| 182 | 73.0 |
| 227 | 73.0 |
| 272 | 74.0 |
| 317 | 74.0 |
| 362 | 74.0 |

No change in the shade of the solution observed in the presence of hypochlorite. After a period of about five hours, approximately 27.6 times more dyestuff identified as Preparative Example II remained in the sodium hypochlorite sanitizing solution than the dyestuff identified as FD&C Blue No. 1. After a period of about one hour, approximately 3.3 times more dyestuff identified in Preparative Example II remained in trichloroisocyanuric acid sanitizing solution than the dyestuff identified as FD&C Blue No. 1.

EXAMPLE 3

A dual compartment automatic dispensing sanitizer for tank and bowl toilets was prepared as follows. A dye-surfactant cake was prepared by heating together 2.0 g of the dye from Preparative Example I having the formula

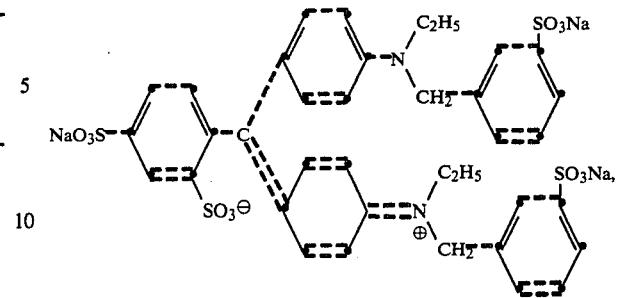

33.0 g of anhydrous sodium sulfate, and 33.0 g of Emulphogene ® TB-970 (GAF Corp.), a commercial tridecyloxypoly(ethyleneoxy)ethanol surfactant, to form a uniform mixture. The molten mixture was placed into a form and cooled to obtain a solid cake. The cake was inserted into one compartment and a cake containing a trichloroisocyanurate sanitizing agent was placed in the second compartment. Then the assembled dispenser was placed into the tank of a conventional tank and bowl flush toilet. After several flushing cycles, the sanitizing solution remaining in the bowl when the flushing cycle was completed remained blue until the next flush. The time between flushes varied from several minutes to over six hours. A similar dual compartment automatic dispensing sanitizer for tank and bowl toilets was prepared substituting the dyestuff FD&C Blue No. 1 for the dyestuff indicated above. The blue color in the sanitizing solution remaining in the bowl when the flushing cycle was completed, faded more rapidly than the dyestuff from Preparative Example I and after six hours, the solution was colorless.

We claim:

1. A triphenylmethane compound having the structural formula

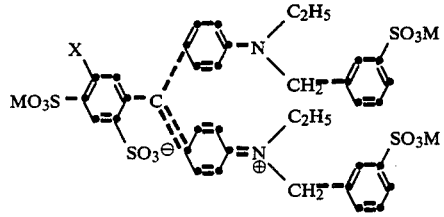

in which:
M represents an alkali metal cation, an ammonium ion or an alkaline earth metal cation; and
X represents hydrogen or hydroxy.

2. A triphenylmethane compound according to claim 1 wherein X is hydrogen.

3. A triphenylmethane compound according to claim 1 wherein X is hydroxy.

* * * * *